United States Patent [19]

Vukovic

[11] 4,369,768
[45] Jan. 25, 1983

[54] ARTHROSCOPE

[76] Inventor: Marko Vukovic, 2052 Lincoln Park West, Chicago, Ill. 60614

[21] Appl. No.: 173,952

[22] Filed: Jul. 30, 1980

[51] Int. Cl.³ .............................................. A61B 1/06
[52] U.S. Cl. ...................................................... 128/6
[58] Field of Search ................................ 128/6, 3–5, 128/7–9, 303.15

[56] References Cited

U.S. PATENT DOCUMENTS

| | | | |
|---|---|---|---|
| 4,024,858 | 5/1977 | Chikama | 128/4 |
| 4,167,944 | 9/1979 | Banko | 128/6 X |
| 4,178,920 | 12/1979 | Cawood, Jr. et al. | 128/6 X |
| 4,217,891 | 8/1980 | Carson | 128/6 |
| 4,261,346 | 4/1981 | Wettermann | 128/6 |

FOREIGN PATENT DOCUMENTS 201775 8/1907 Fed. Rep. of Germany .......... 128/8

Primary Examiner—Mickey Yu
Attorney, Agent, or Firm—Robert E. Browne; Stephen R. Arnold

[57] ABSTRACT

An improved diagnostic and operative arthroscope is described having an extended eye piece and optical channel, an instrument channel, light source and irrigation channel. The functional channels and light source are secured in parallel and covered by a sheath so as to form a generally oval shape in cross-section, presenting a low profile and enabling the use of the arthroscope with incisions of relatively smaller size.

2 Claims, 4 Drawing Figures

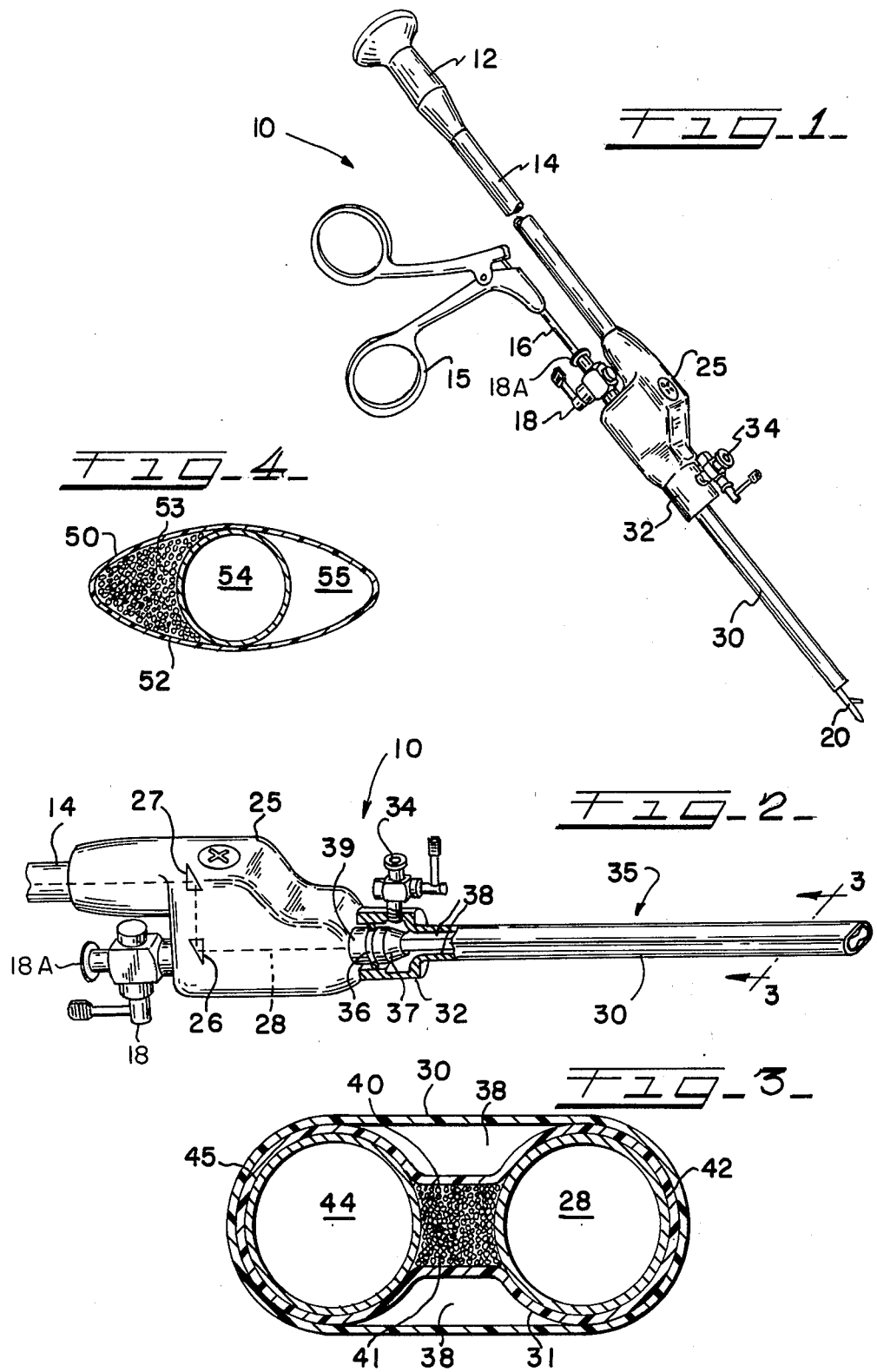

ARTHROSCOPE

DESCRIPTION

1. Technical Field

This invention relates to surgical instruments and, in particular, to a diagnostic and operative arthroscope for use in intra-articular surgery.

2. Background of the Prior Art

Surgical instruments in the nature of endoscopes have been known and used in the art for some time. However, even as lately as the last decade, such instruments were used chiefly for diagnostic and operative procedures involving pleuric and abdominal cavities and were known as laparoscopes. More recently, endoscopes have been utilized in diagnostic and operative procedures involving the urinary tract. Such instruments are known as cystoscopes. As surgeons became more familiar with the advantages of diagnostic and operative procedures utilizing endoscopes, it became apparent that other surgical operations could benefit through the use of the endoscopes. In particular, the many risks associated with knee surgery can be minimized through the use of an endoscope or, as known for this particular application, arthroscope. Up to now, arthroscopes have not been significantly different from other endoscopes such as the cystoscope or the laparoscope, differing principally in the surgical instruments used in operating on the knee.

Arthroscopes of the prior art have included a lens system for providing visual contact with the affected area, as well as a source of light for illuminating the desired area. Of late, fiber optics has been utilized for the transmission of a light beam to the area being viewed. Operative arthroscopes also generally include channels for irrigation and instruments. All of these functional devices are encased in a round sheath which is inserted into an incision near the knee area for diagnosis or operation, as required, and the particular diagnostic or operative procedure desired is followed.

In making the incision for the insertion of the arthroscope sheath, it is known that good surgical procedure requires a small incision, the smaller the better. Small incisions require a short recuperative period, generally speaking, in direct proportion to the size of the incision. With a large incision and correspondingly longer period of time for the knee and leg to be immobilized, a greater atrophy of the leg muscles is abserved. Thus, a longer period of recuperation is required to return the leg muscles and knee to full strength and mobility. In addition, a large incision invites a greater prospect of infection to the surrounding tissues.

SUMMARY OF THE INVENTION

Therefore, an object of the subject invention is an endoscope having decreased clearance height, thereby allowing a smaller incision to be made for insertion of the arthroscope in the knee area.

Still another object of the subject invention is an arthroscope having a removable instrument sheath for providing a fluid irrigation channel about the functional channels.

A further object of the subject invention is a diagnostic arthroscope requiring a minimal incision or surgical cut.

These and other objects are attained in accordance with the subject invention wherein there is provided an arthroscope for use both as a diagnostic instrument and an operative instrument. When used as an operative instrument, the arthroscope of the subject invention has an optical channel extending from an eye piece through a handset and, via a conduit, into the incision for viewing the affected area about the knee. A second channel extends through the handset and runs parallel with the optical channel for introducing the various instruments into the incision for surgical operations within the body. Typical instruments which may be used in connection with the arthroscope of the subject invention include probes, knives, drills and saws. Between the instrument channel and the viewing channel are a plurality of fiber optic strands for transmitting light from a source within the handset and directing the light to that part of the incision desired to be inspected. In cross-section, this portion of the arthroscope assembly resembles a dumbbell. A sheath surrounds and envelopes the outer ends of the instrument channel and viewing channel, providing a fluid-tight irrigation channel for the flow of irrigation fluid into the incision. With the sheath in place, the operative arthroscope assembly is complete and, in cross-section, is generally oval, having two opposing flat sides to provide a low profile probe which permits smaller incisions, while retaining the full manneuverability and capability generally associated with the use of arhtroscopes. The sheath is removable to allow the use of the viewing channel and fiber optics as a diagnostic instrument. An alternative embodiment of the subject invention, i.e., a low profile diagnostic probe comprising a viewing channel, light source and irrigation channel, can also be used.

BRIEF DESCRIPTION OF SEVERAL VIEWS OF DRAWINGS

Further objects of the invention together with additional features contributing thereto and advantages accuring therefrom will become apparent from the following description of one embodiment of the invention when read in conjunction with the accompanying drawings wherein:

FIG. 1 is a perspective view of the arthroscope of the subject invention;

FIG. 2 is a further perspective view of the arthroscope of the subject invention not showing the eye piece and having a partial cut-away view to better show the irrigation inlet;

FIG. 3 is a cross-section taken along lines 3—3 of FIG. 2 showing the different functional channels of the operative arthroscope of the subject invention; and, FIG. 4 is a cross-section of a second embodiment of the subject invention showing the different channels within a diagnostic arthroscope.

DETAILED DESCRIPTION

Referring now to FIG. 1 there is shown one embodiment of the arthroscope 10 of the subject invention having an extended eye piece 12, a viewing conduit 14 leading into handset 25 which contains a series of lenses, as will be described. The handset 25, as well as the viewing conduit 14 and eye piece 12, is generally of polished metal, preferably chrome-plated; however, other durable materials such as plastic or the like may be used as desired. The handset 25 allows for the entry of surgical instruments, such as shown in 15, into the handset for manipulation within an incision. The instrument 15 generally comprises a shaft 16, with manipulating means at the operator end. The shaft 16 enters the handset 25 through entryway 18A for providing a fluid-tight connection at that point to a clear-passage valve 18. The probe tip 20 of the instrument 15 is controlled in its particular function by the manipulating means as known in the art.

The operative end of the arthroscope 10 of the subject invention comprises a sheath 30 forming an irrigation channel about the operative and diagnostic or probe portion 35 of the arthroscope. The irrigation channel 38, as shown in FIG. 2, conducts irrigation fluid through valve 34 from an outside source (not shown). Sheath 30, forming the irrigation channel 38, comprises a flexible plastic skin which conforms to the probe portion 35 of the arthroscope and forms a fluid-tight seal on the insertion of base 32 of the sheath 30 over O-ring 36, seated in circumferential slot of connector fitting 39. Connector fitting 39 has a tapered outer end portion 37 to facilitate the influx of irrigation fluid through valve 34 into channel 38.

The optical system of the arthroscope 10 of the subject invention, as already stated, has an extended eye piece 12 for assurances of aseptic technique. The line-of-sight of the subject optical system through handset 25 is depicted in FIG. 2 by dotted lines 28 and can be seen to be refracted through prisms 26 and 27 for directing the line-of-sight parallel with the functional channels in the probe portion 35. As seen in FIG. 3, the conduit or channel 42 provides for the line-of-sight 28 within the probe portion 35 of the arthroscope 10 of the subject invention.

As shown in FIG. 3, with sheath 30 in place about the probe portion 35 of the arthroscope 10, the cross-sectional shape appears as an oval, much in the nature of a racetrack. An instrument channel 44 formed by conduit 45 and the viewing channel 28 formed by conduit 42 are separated by fiber optic channel 40 wherein a plurality of fiber optic strands 41 are secured and retained in place through a sleeve 31 which may be plastic or metal, as desired, covering conduits 42 and 45 and forming the entire assembly into a dumbbell shape or, more precisely, two spherical objects connected by a thinner central portion.

The flexible sheath 30 encases the entire operative assembly, forming the irrigation channels 38 on either side of the fiber optic channel. The racetrack shape resulting from the insertion of the sheath 30 over the probe portion 35 of the arthroscope 10, in general, has a straight-away portion or distance between the centers of conduits 42 and 45 of between two to four times the radius of the conduits 42 and 45. Such a relationship gives the sheath assembly a low profile or flattened oval shape which permits the entry of the sheath portion of the arthroscope into smaller incisions for surgical procedures in and about the knee. As stated above, small incisions mean shorter recovery time and fewer chances of complications due to infection of surrounding tissues and the like.

FIG. 4 shows an alternative embodiment of the subject invention for use in diagnostic procedures only. This embodiment has a cylindrical channel 54 encompassed by a second and third channel formed through enveloping channel 54 with a rigid ellipse-shaped tube. Channel 54 comprises a viewing channel providing a line-of-sight to the injured area from the eye piece, similar to the manner shown in FIG. 1. Channel 55, formed by the viewing channel 54 and one side of the ellipse, is an irrigation channel which may be supplied with irrigation fluid from a valve integral with the handset. Channel 52 provides the fiber optic strands 53 for conducting light for illuminating the affected area for viewing through channel 54. As with the diagnostic and operative instrument shown in FIGS. 1-3, the diagnostic instrument depicted in cross-section in FIG. 4 has a low profile and can be inserted through incisions of lesser magnitude, thereby allowing faster healing and smaller scars with less complications.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out the invention, but that the invention will include all embodiments falling within the scope of the appended claims.

I claim:

1. An arthroscope for use in diagnostic and surgical procedures involving an injured area, such as the knee and surrounding tissue, comprising:

a body portion;

a probe portion;

a viewing portion secured to generally opposite sides of said body portion, said arthroscope configured to provide a line-of-sight from said viewing portion to said probe portion provided through said body portion, said probe portion including a tubular instrument conduit for carrying a selected surgical instrument for operative procedures in the injured area, and a tubular viewing conduit of substantially the same diameter through which the injured area proximate to the probe tip may be viewed; said instrument conduit and said viewing conduit secured parallel to one another, said conduits secured to each other along their length and separated by a hollow joining member to form a substantially dumbbell-shaped cross-section;

a removable sheath configured to surround said probe along its length, said sheath being made of a compliant material and configured slightly undersized with respect to the transverse dimensions of said probe, so that said sheath when affixed over said probe conforms to the exterior of said instrument and viewing conduits in a fluid-tight manner, but leaving a pair of clear channels between said sheath and said joining member;

means for sealably connecting the instrument-insertion end of said instrument conduit to a source of irrigating liquid, so that with said sheath removed and no instrument in said instrument conduit, said instrument conduit may serve as an alternate irrigation channel for purely diagnostic observation;

clear passage valve means disposed in communication with said instrument conduit with the passage axis of said valve means aligned with the center axis of said instrument conduit, so that with said valve in the open position an inserted instrument can pass the length of said instrument conduit unobstructed by said valve means, and so that with said instrument removed, actuation of said valve means alternatively to an open or closed condition controls the flow of irrigation liquid when said instrument channel is serving as said alternate irrigation channel;

second valve means for connecting said sheath to a source of irrigation fluid to control the supply of said irrigating fluid to the area under inspection through said pair of clear channels; and, illumination means in said probe for illuminating the area to be inspected, said illumination means including a plurality of fiber optic strands disposed within said hollow joining member so as to convey light from a source thereof to the tip of said probe.

2. An arthroscope for use in diagnostic and surgical procedures involving an injured area, such as the knee and surrounding tissue, comprising:

a body portion;

a probe portion;

a viewing portion secured to generally opposite sides of said body portion, said arthroscope configured to provide a line-of-sight from said viewing portion to said probe portion provided through said body portion, said probe portion including a tubular instrument conduit for carrying a selected surgical instrument for operative procedures in the injured area, and a tubular viewing conduit of substantially the same diameter through which the injured area proximate to the probe tip may be viewed; said instrument conduit and said viewing conduit secured parallel to one another, said conduits secured to each other along their length and separated by a hollow joining member to form a substantially dumbbell-shaped cross-section;

a removable sheath configured to surround said probe along its length, said sheath being made of a compliant material and configured slightly undersized with respect to the transverse dimensions of said probe, so that said sheath when affixed over said probe conforms to portions of the exterior of said instrument conduit and said viewing conduit in a fluid-tight manner, but leaving a pair of clear channels between said sheath and said joining member; and, means for connecting at least one of said clear channels to a source of irrigation liquid, said clear channels directing the flow of said liquid between said source and said injured area.

* * * * *